US00PP20452P2

(12) United States Plant Patent
Hanes

(10) Patent No.: US PP20,452 P2
(45) Date of Patent: Nov. 3, 2009

(54) ***PELARGONIUM* PLANT NAMED 'AMRI SAL09'**

(50) Latin Name: ***Pelargonium hortorum* (L.)** *L' Herit. ex Ait*
Varietal Denomination: Amri Sal09

(75) Inventor: Mitchell Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 12/218,885

(22) Filed: Jul. 18, 2008

(51) Int. Cl.
*A01H 5/00* (2006.01)

(52) U.S. Cl. ..... Plt./327

(58) Field of Classification Search ..... Plt./327
See application file for complete search history.

*Primary Examiner*—June Hwu
(74) *Attorney, Agent, or Firm*—S. Matthew Edwards

(57) ABSTRACT

A new *Pelargonium* plant named 'Amri Sal09,' particularly distinguished by the salmon flower color with soft pink margins, medium leaf zonation, round and semi-compact yet vigorous plant habit, with good garden performance.

1 Drawing Sheet

Latin name of the genus and species of the plant claimed: *Pelargonium hortorum* (L.) *L' Herit. ex Ait.*

Varietal denomination: 'Amri Sal09'.

BACKGROUND OF THE NEW PLANT

The present invention comprises a new *Pelargonium,* botanically known as *Pelargonium hortorum,* and hereinafter referred to by the variety name 'Amri Sal09.'

'Amri Sal09' is a product of a planned breeding program. The new cultivar 'Amri Sal09' has salmon flower color with soft pink margins, medium leaf zonation, round and semi-compact yet vigorous plant habit, with good garden performance.

'Amri Sal09' originated from a hybridization in a controlled breeding program in Gilroy, Calif. USA. The female parent was an unpatented hybrid seedling identified as '9716-1' with light salmon color. '9716-1' has a lighter salmon color, lighter leaf zonation, and a smaller flower size than 'Amri Sal09.'

The male parent of 'Amri Sal09' was an unpatented hybrid seedling identified as '9675-1' with a salmon color. '9675-1' has less plant vigor and is later to flower than 'Amri Sal09.'

'Amri Sal09' was selected as one flowering plant within the progeny of the stated cross in 2004 in a controlled environment in Gilroy, Calif. USA.

The first act of asexual reproduction of 'Amri Sal09' was accomplished when vegetative cuttings were propagated from the initial selection in August 2004 in a controlled environment in Gilroy, Calif. USA.

Horticultural examination of plants grown from cuttings of the plant initiated in August 2004 in Gilroy, Calif. USA, and continuing thereafter, has demonstrated that the combination of characteristics as herein disclosed for 'Amri Sal09' are firmly fixed and are retained through successive generations of asexual reproduction.

'Amri Sal09' has not been observed under all possible environmental conditions. The phenotype may vary significantly with variations in environment such as temperature, light intensity and day length.

Plant Breeder's Rights for this cultivar were applied for in Canada on Aug. 23, 2007 and in Germany on Jul. 2, 2007. 'Amri Sal09' has not been made publicly available more than one year prior to the filing of this application.

BRIEF DESCRIPTION OF THE NEW VARIETY

The accompanying photographic drawing shows typical flower and foliage characteristics of 'Amri Sal09' with colors being as true as possible with an illustration of this type. The photographic drawing shows a flowering potted plant of the new variety and a close-up of the flowers.

DETAILED BOTANICAL DESCRIPTION

The measurements were taken in Gilroy, Calif. USA, in August 2007 on plants that were growing in a greenhouse in one gallon pots. Cultures of these plants started in the approximately March. The plants were approximately 4–5 months old.

Color Chart used: Royal Horticultural Society Colour Chart (R.H.S.) 2001

BRIEF SUMMARY OF INVENTION

The following observations, measurements, and comparisons describe plants grown in a greenhouse in Gilroy, Calif., USA. The following traits have been repeatedly observed and are determined to be basic characteristics of the new variety. The combination of these characteristics distinguishes this *Pelargonium* as a new and distinct variety.

TABLE 1

DIFFERENCES BETWEEN THE NEW VARIETY AND A SIMILAR VARIETY

| | 'Amri Sal09' | 'Americana Light Salmon' (U.S. Plant Pat. No. 7,936) |
|---|---|---|
| Flower color | Deeper orange | Lighter orange |
| Petaloids | Fewer | More |
| Foliage | Larger size leaf, darker zone | Smaller size leaf, lighter zone |
| Plant size | Larger plant | Smaller plant |

Plant:

*Form, growth and habit.*—Upright and rounded growth habit. Well-branched.

*Plant height.*—18–22 cm.

*Plant height* (*inflorescence included*).—24–26 cm.
*Plant width.*—18–20 cm.

Foliage:
*Arrangement.*—Alternate, simple.
*Immature, leaf color, upper surface.*—RHS 146A, with a zone of RHS 187A but lighter Lower surface: RHS 147C.
*Mature, leaf color, upper surface.*—RHS 146A Lower surface: RHS 147C.
*Length.*—5.0–5.3 cm.
*Width.*—8.5–10 cm.
*Shape.*—Orbicular.
*Base shape.*—Reniform.
*Apex shape.*—Rounded.
*Margin.*—Very slightly lobed; irregularly crenate.
*Texture, both surfaces.*—Hirsute, glandular hairs of approximately RHS 25B.
*Color of zone.*—Closest to RHS 187A, but a little darker.
*Width of zone.*—1.5–2.0 cm.
*Color of veins, upper surface.*—Indistinct.
*Color of veins, lower surface.*—RHS 146C.
*Petioles color.*—RHS 146C.
*Petioles length.*—5.7–6.3 cm.
*Diameter of petiole.*—0.3 cm.
*Texture.*—Hirsute.

Stem:
*Color of stem.*—RHS 146D.
*Length of stem.*—9–10 cm.
*Diameter.*—0.6–0.8 cm.
*Length of internodes.*—1.5–2 cm.
*Texture.*—Hirsute.

Inflorescence:
*Type.*—An umbel composed of 30–35 flowers and buds.
*Average quantity of umbels per plant.*—30.
*Umbel diameter.*—10–12 cm.
*Umbel depth.*—10–12 cm.
*Color of peduncle.*—RHS 146C.
*Length of peduncle.*—12–14 cm.
*Peduncle diameter.*—0.4–0.5 cm.
*Texture.*—Hirsute; glandular hairs of approximately RHS 25B.
*Pedicel color.*—RHS 144B.
*Length of pedicel.*—2–2.8 cm.
*Diameter of pedicel.*—0.2 cm.
*Texture.*—Glandular hairs of approximately RHS 25B.

Corolla:
*Form.*—Polypetalous, overlapping.
*Number of petals.*—7–9.
*Width of flower.*—5–5.5 cm.
*Depth of flower.*—1.0–1.5 cm.
*Color upper petals, upper surface.*—Immature flowers: RHS 65D ground color; overlaid with slight mottling of RHS 41C at basal and midpetal, RHS 52C margins and RHS 41B veins Mature flowers: RHS 65D ground color fading to RHS 38D; overlaid with slight mottling of RHS 52C basally and at midpetal; with RHS between RHS 54A and B at the margins and RHS 41C veins.
*Color upper petals, lower surface.*—RHS 38C.
*Length of upper petals.*—2.5–2.6 cm.
*Width of upper petals.*—2.0–2.1 cm.
*Petal shape.*—Obovate.
*Apex shape.*—Rounded.
*Margin.*—Entire.
*Petal texture.*—Papillose, both sides.
*Number of petaloids.*—1–3.
*Color of petaloids.*—Same as petals.
*Average length of petaloids.*—1.3 cm.
*Average width of petaloids.*—0.7 cm.
*Duration of flowering.*—Continuous flowering throughout the Summer.
*Lastingness of flowers.*—About one week.

Bud (when sepals first divide):
*Color.*—RHS 38C with slight stripes of RHS 41B.
*Length.*—1.1–1.3 cm.
*Width.*—0.6–0.7 cm.
*Shape.*—Elliptical.
*Number of sepals.*—5, fused at the base.
*Color of sepals.*—RHS N144C.
*Length of sepals.*—1.0–1.2 cm.
*Width of sepals.*—0.2–0.3 cm.
*Sepal shape.*—Lanceolate to linear.
*Apex shape.*—Acute.
*Margins.*—Entire.
*Texture, upper surface.*—Smooth.
*Lower surface.*—Glandular hairs; some pilose at margins.

Reproductive organs:
*Pistil.*—1.
*Length.*—0.8–1.1 cm.
*Style color.*—RHS N155B but whiter.
*Style length.*—0.2–0.3 cm.
*Stigma color.*—RHS 52A.
*Number of anthers.*—8.
*Length filaments.*—0.7–0.8 cm.
*Color of filaments.*—RHS N155B but whiter.
*Pollen amount.*—Moderate.
*Color of pollen.*—RHS 47B.
*Fertility/seed set.*—Not observed on this hybrid.

Disease/pest resistance: Disease resistance and/or susceptibility has not been observed on this hybrid.

What is claimed is:

1. A new and distinct variety of *Pelargonium* plant named 'Amri Sal09,' substantially as illustrated and described herein.

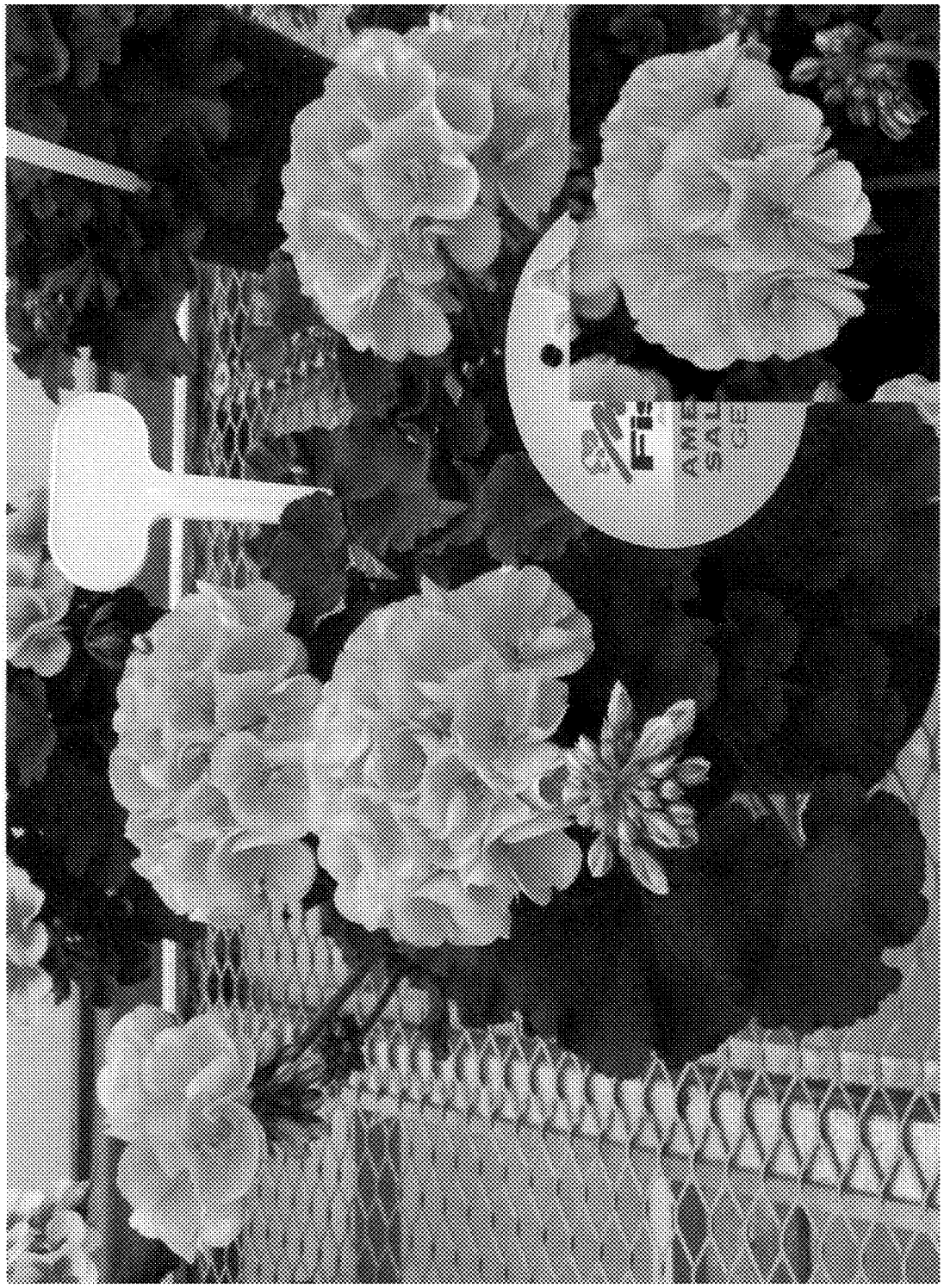

* * * * *